United States Patent [19]

Sie

[11] Patent Number: 4,594,172
[45] Date of Patent: Jun. 10, 1986

[54] PROCESS FOR THE PREPARATION OF HYDROCARBONS

[75] Inventor: Swan T. Sie, Amsterdam, Netherlands

[73] Assignee: Shell Oil Company, Houston, Tex.

[21] Appl. No.: 706,437

[22] Filed: Feb. 27, 1985

[30] Foreign Application Priority Data

Apr. 18, 1984 [NL] Netherlands ............... 8401253

[51] Int. Cl.$^4$ .................................... C10M 7/16
[52] U.S. Cl. .......................................... 252/55
[58] Field of Search ..................... 585/3; 252/55

[56] References Cited

U.S. PATENT DOCUMENTS 4,520,815  5/1985  Owen et al. .................. 585/3 X

FOREIGN PATENT DOCUMENTS 546432  9/1957  Canada ......................... 252/55

*Primary Examiner*—Ferris H. Lander
*Attorney, Agent, or Firm*—Kimbley L. Muller

[57] ABSTRACT

Syngas is subjected to Fischer-Tropsch synthesis over a special Co/Zr/SiO$_2$ catalyst and the C$_{10}$–C$_{19}$ fraction of the synthesized product is converted into XHVI lub oil by treating with an organic peroxide.

18 Claims, No Drawings

PROCESS FOR THE PREPARATION OF HYDROCARBONS

FIELD OF THE INVENTION

The invention relates to a process for the preparation of high-viscosity-index lubricating oils.

BACKGROUND OF THE INVENTION

High-viscosity-index lubricating oils are used on a large scale for the formulation of multi-purpose lubricating oils. They can be prepared, for instance by peroxidation of linear paraffins having at least 10 and at most 19 carbon atoms per molecule (hereinafter referred to as "linear $C_{10}$–$C_{19}$ paraffins"). The peroxidation should be carried out by contacting the paraffins at an elevated temperature with an organic peroxide of the general formula R-O-O-R$^1$, wherein R and R$^1$ represent alkyl, aryl or acyl moieties. Linear $C_{10}$–$C_{19}$ paraffins, together with branched $C_{10}$–$C_{19}$ paraffins are found in light mineral oil fractions, such as kerosine and gas oil fractions. The paraffins can be separated from said mineral oil fractions by cooling. From the paraffin mixtures obtained the desired linear paraffins can be isolated by way of fractional crystallization or complexing with urea. The linear $C_{10}$–$C_{19}$ paraffins thus obtained are usually contaminaed with sulfur- and nitrogen compounds from the mineral oil, and also cyclic compounds. Preparatory to being suitable for use as feed for the preparation by peroxidation of high-viscosity-index lubricating oils, the $C_{10}$–$C_{19}$ paraffins should be freed from these contaminants.

Linear $C_{10}$–$C_{19}$ paraffins which can suitably be used as starting material for the preparation by peroxidation of high-viscosity-index lubricating oils may also be synthesized starting from a mixture of carbon monoxide and hydrogen. In this process (which is termed a Fischer-Tropsch synthesis) a $H_2$/CO mixture is contacted at elevated temperature and pressure with a catalyst comprising one or more metals from the iron group together with one or more promoters and a carrier material. The preparation of these catalysts can suitably be carried out by the known techniques, such as precipitation, impregnation, kneading and melting. As compared with waxy light mineral oil fractions, the products prepared by the Fischer-Tropsch synthesis have the advantage that they contain virtually no sulfur- and nitrogen compounds and cyclic compounds. Nevertheless there is a drawback to using the products obtained over the usual Fischer-Tropsch catalysts for the preparation of high-viscosity-index lubricating oils, which drawback is connected with their composition. For the $C_{10}$–$C_{19}$ compounds are made up to a considerable extent of branched paraffins, branched and unbranched olefins, and oxygen-containing compounds.

Recently there has been found a class of Fischer-Tropsch catalysts which have the property of yielding a product wherein the $C_{10}$–$C_{19}$ compounds consist virtually exclusively of linear paraffins. The Fischer-Tropsch catalysts belonging to the above-mentioned class contain silica, alumina or silica-alumina as carrier material, and cobalt together with zironium, titanium and/or chromium as catalytically active metals, in such quantities that per 100 parts by weight (pbw) of carrier material, the catalysts comprise 3–60 pbw of cobalt and 0.1–100 pbw of zirconium, titanium, and/or chromium. The catalysts are prepared by depositing the metals involved on the carrier material by kneading and/or impregnation. For further information concerning the preparation of these catalysts by kneading and/or impregnation reference may be made to Netherlands patent application No. 8301922, recently filed by the Applicant. Considering the composition of the product prepared over the cobalt catalysts it is extremely attractive to separate from said product a light fraction substantially consisting of $C_{10}$–$C_{19}$ paraffins and to convert at least part of this light fraction by peroxidation into a product containing the desired high-viscosity-index lubricating oil.

SUMMARY OF THE INVENTION

The present patent application therefore relates to a process for the preparation of a high-viscosity-index lubricating oil, in which a mixture of carbon monoxide and hydrogen is converted into a mixture of hydrocarbons substantially consisting of linear paraffins, by contacting it at elevated temperature and pressure with a catalyst comprising 3–60 pbw of cobalt and 0.1–100 pbw of at least one other metal selected from the group consisting of zirconium, titanium and chromium per 100 pbw of silica, alumina or silica-alumina carrier which catalyst has been prepared by kneading and/or impregnation, in which from the mixture of paraffins thus prepared a light fraction is separated which consists substantially of $C_{10}$–$C_{19}$ paraffins, and in which at least part of said light fraction is converted into a product comprising the desired high-viscosity-index lubricating oil by treating it at an elevated temperature with a peroxide of the general formula R-O-O-R$^1$, wherein R and R$^1$ represent alkyl, aryl or acyl moieties.

DETAILED DESCRIPTION OF THE INVENTION

In the process according to the invention the starting material should be a $H_2$/CO mixture. Suitable $H_2$/CO mixtures can be prepared by gasifying of heavy carbonaceous materials, such as coal and residual mineral oil fractions. It is preferred to start from a $H_2$/CO mixture which has been obtained by the steam reforming or partial oxidation of light hydrocarbons, in particular natural gas.

In the process according to the invention preference is given to the use of the cobalt catalysts which form the subject matter of Netherlands patent application No. 8301922. These are catalysts which satisfy the relation:

$$(3+4R) > (L/S) > (0.3+0.4 R),$$

wherein
- L = the total quantity of cobalt present on the catalyst, expressed as mg Co/ml catalyst,
- S = the surface area of the catalyst, expressed as m$^2$/ml catalyst, and
- R = the weight ratio of the quantity of cobalt deposited on the catalyst by kneading to the total quantity of cobalt present on the catalyst.

In a preferred embodiment, th cobalt catalysts are prepared by one of the three procedures described hereinafter:

(a) first cobalt is deposited in one or more steps by impregnation and subsequently the other metal is deposited in one or more steps, also by impregnation, (b) first the other metal is deposited in one or more steps by impregnation and subsequently the cobalt is deposited in one or more steps, also by impregnation, and (c) first cobalt is deposited in one or more steps by kneading and subsequently the other metal is deposited in one or more steps by impregnation.

Preferably, the cobalt catalysts contain 15–50 pbw of cobalt per 100 pbw of carrier. The preferred quantity of other metal present in the cobalt catalysts depends on the way in which this metal has been deposited. In the case of catalysts where first cobalt has been deposited on the carrier, followed by the other metal, preference is given to catalysts containing 0.1–5 pbw of the other metal per 100 pbw of carrier. In the case of catalysts where first the other metal has been deposited on the carrier, followed by the cobalt, preference is given to catalysts containing 5–40 pbw of the other metal per 100 pbw of carrier. Preference is given to zirconium as the other metal and to silica as carrier material.

The conversion of the $H_2/CO$ mixture is preferably carried out at a temperature of 125°–350° C. and a pressure of 5–100 bar and in particular at a temperature of 175°–275° C. and a pressure of 10–75 bar. The peroxidation treatment which according to the invention is applied to at least part of the light fraction of the product prepared over the cobalt should be carried out by contacting the fraction to be treated at an elevated temperature with an organic peroxide of the genera formula $R-O-O-R^1$, wherein R and $R^1$ represent alkyl, aryl, or acyl moieties. Preference is given to di-tert.alkyl peroxides with 8–20 carbon atoms per molecule, in particular di-tert.butyl peroxide. The quantity of peroxide to be used may vary within wide limits. Usually it is at least 10% w, calculated on the paraffin fraction to be treated. The maximum amount of peroxide that can be used is largely dependent on the properties of the paraffins and the desired properties of the lubricating oil to be prepared. Generally the quantity of peroxide to be used amounts to not more than 150% w, and in particular not more than 100% w, calculated on the paraffin fraction to be treated. Although the reaction time and reaction temperature may vary within wide ranges, they are usually chosen between 5 minutes and 10 hours, and between 100° and 225° C. The peroxide treatment is preferably carried out at such a reaction time and such a reaction temperature that at the moment that the treatment is terminated there has been achieved at least a 90%w, and in particular at least a 95%w, decomposition of the peroxide. The reaction time is dependent on the decomposition rate of the peroxide involved and may be shorter with higher reaction temperatures used. The peroxide treatment may be carried out in a single step, in which a single portion consisting of the total required amount of peroxide is added to the paraffin fraction, or it may be carried out in several steps, in which at each step a portion of the required quantity of peroxide is added to the reaction product. In the process according to the invention the peroxide treatment of the paraffin fraction is preferably carried out in several steps. For instance it may suitably be done as follows. The light paraffin fraction is treated with peroxide, the peroxide-treated product is divided by distillation into a light fraction and a heavy fraction whose initial boiling point lies above the final boiling point of the light paraffin fraction to be peroxidated, and the heavy fraction is treated once or several times with peroxide. The multi-step peroxide treatment of the light paraffin fraction may also suitably be carried out as follows. The light paraffin fraction is treated with peroxide, the peroxide-treated product is divided by distillation into a light fraction and a heavy fraction whose initial boiling point lies above the final boiling point of the light paraffin fraction to be peroxidated. The light fraction is treated with peroxide again, and optionally the process is repeated several time more. The heavy fractions obtained from the peroxide-treated products by distillation are mixed together, and the mixture is in its turn subjected once or several times to peroxide treatment. Thus, starting from linear $C_{10}-C_{19}$ paraffins, a high-viscosity-index lubricating oil can be prepared according to the invention virtually quantitatively.

In the process there is separated from the product prepared over the cobalt catalyst a fraction in which the paraffins contain substantially at least 10 and at most 19 carbon atoms, and from this $C_{10}-C_{19}$ fraction at least a portion is converted by peroxidation into high-viscosity-index lubricating oil. The $C_{20+}$ fraction obtained in the hydrocarbon synthesis over the cobalt catalyst can also be used for preparing high-viscosity-index lubricating oil. There are various methods to achieve this. Subjecting the $C_{20+}$ fraction to catalytic hydro-isomerization yields a product from which a high-viscosity-index lubricating oil can be separated. Subjecting the $C_{20+}$ fraction to mild thermal cracking yields a mixture consisting substantially of linear olefins. Subjecting at least part of these olefins to peroxidation as described hereinbefore also leads to a product from which a high-viscosity-index lubricating oil can be separated. In the preparation of high-viscosity-index lubricating oil starting from the $C_{20+}$ fraction of the product prepared over the cobalt catalyst it is also suitable to combine catalytic-hydroisomerization and peroxidation. For instance, from the product obtained by catalytic hydro-isomerization a high-viscosity-index lubricating oil can be separated, which lubricating oil can be subsequently be peroxidated to boost its viscosity. The peroxidation may also be applied to the total of liquid product obtained in the catalytic hydro-isomerization. Finally, the preparation of high-viscosity-index lubricating oil starting from the $C_{20+}$ fraction of the product prepared over th cobalt catalyst can also be carried out by subjecting part of the $C_{20+}$ fraction to catalytic hydro-isomerization in order to prepare lubricating oil, and subjecting the remainder of the $C_{20-}$ fraction to mild thermal cracking in order to prepare linear olefins, and then subjecting a mixture of the lubricating oil and linear olefins thus prepared to peroxidation.

In the process according to the invention part of the $C_{19-}$ fraction of the product prepared over the cobalt catalyst can be used to prepare a lubricating oil by a different method. To achieve this, the fraction concerned can be subjected to dehydrogenation or chlorination followed by dehydrochlorination or steam cracking followed by oligomerization to prepare a mixture of linear olefins, and these olefins can be converted into a lubricating oil by thermal or Friedel-Crafts plymerization.

Thus far in the present patent application there has only been mention of the use of the product obtained over the cobalt catalyst as feed for the preparation of high-viscosity-index lubricating oil. According to the invention, to this end at least part of the $C_{10}-C_{19}$ fraction should be subjected to peroxidation. Optionally the entire $C_{10}-C_{19}$ fraction can be converted in this manner. In addition as described hereinbefore, the $C_{20+}$ fraction can be used partly or wholly for preparing high-viscosity-index lubricating oil. In view of the special composition of the product obtained over the cobalt catalyst which consists virtually completely of linear paraffins, this product is also excellently suitable for a number of other uses which can be combined with the process according to the invention. To this end either the $C_{20+}$ fraction or part of the $C_{19-}$ fraction can be used.

In addition to the use of the $C_{10}$–$C_{19}$ fraction according to the invention for the preparation of high-viscosity-index lubricating oil by peroxidation, the $C_{19-}$ fraction is also very suitable for the following uses.

1. From the $C_{19-}$ fraction a mixture of lower olefins substantially consisting of ethene can be prepared by steam cracking.

2. From the $C_{10}$–$C_{19}$ fraction linear $C_{10}$–$C_{19}$ olefins which form valuable base materials for the preparation of synthetic detergents can be prepared by dehydrogenation of chlorination followed by dehydrochlorination.

3. The light fractions with a narrow boiling range present in the $C_5$–$C_{11}$ fraction are very suitable, either per se or after a mild hydrogenation or hydro-isomerization aimed at converting minor quantities of olefins and/or oxygen-containing compounds, or introducing some branching, to be used as special solvents. In this connection may be mentioned their use as extracting liquids for oil seeds, as spray oils for insecticides and pesticides, as solvents for medicinal and pharmaceutical purposes as well as their use in the food industry.

In addition to their use as feedstock for the preparation of high-viscosity-index lubricating oils, the $C_{20+}$ fraction can also very suitably be put to the following uses.

1. By mild thermal cracking a mixture of linear higher olefins can be obtained form the $C_{20+}$ fraction, the $C_{10-C20}$ fraction of which mixture forms a valuable base material for the preparation of synthetic detergents.

2. By fractional crystallization valuable solid paraffins can be separated from the C hd $20_+$ fraction.

3. By steam cracking a mixture of lower olefins can be obtained from the $C_{20+}$ fraction, which mixture consists substantially of ethene.

4. By cataytic hydrocracking the $C_{20+}$ fraction can be converted into middle distillates.

The afore-mentioned steam cracking for the preparation of a mixture of lower olefins substantially consisting of ethene may very suitably be carried out at a temperature of 700°–1000° C., a pressure of 1–5 bar abs., a residence time of 0.04–0.5 seconds and in the presence of a quantity of steam which amounts to 20–100%w, calculated on hydrocarbon feed.

The invention is now illustrated with the aid of the following example.

EXAMPLE

Five hydrocarbon synthesis experiments were carried out by using the following catalysts.

Catalyst A

This catalyst comprised 10 pbw of iron, 5 pbw of copper, 2 pbw of potassium and 30 pbw of kieselguhr, and had been prepared by precipitation of iron and copper from an aqueous solution by using potassium carbonate, while kieselguhr was being added.

Catalyst B

This catalyst comprised 97.5 pbw of iron, 2.5 pbw of aluminum and 0.5 pbw of potassium, and had been prepared by melting a mixture of $Fe_3O_4$ and the oxides of aluminum and potassium in an arc.

Catalyst C

This catalyst comprised 100 pbw of cobalt, 5 pbw of thorium oxide, b 7.5 pbw of magnesium oxide and 200 pbw of kieselguhr, and had been prepared by precipitation of cobalt and thorium from an aqueous solution, while kieselguhr was bein added.

Catalyst D

This catalyst comprises 25 pbw of cobalt and 0.9 pbw of zirconium per 100 pbw silica, and had been prepared by kneading a silica carrier in a solution of cobalt nitrate in water, followed by single-step impregnation of the cobalt-loaded carrier with a solution of zirconylchloride in water.

Catalyst E

This catalyst comprised 23 pbw of cobalt and 17 pbw of zirconium per 100 pbw of silica, and had been prepared by three-step impregnation of a silica carrier with a solution of zirconiumtetra n-propoxide in a mixture of n-propanol and benzene, followed by single-step impregnation of the zirconium-loaded carrier with a solution of cobalt nitrate in water.

During the preparation of Catalysts D and E, such a quantity of solution was used in each impregnation step that its volume corresponds substantially with the pore volume of the carrier. After each impregnation step the solvent was removed by heating, and the material was calcined at 500° C. When a kneading step was used, the quantity of solution used had a volume substantially corresponding with 150% of the pore volume of the carrier. When a kneading step was used, the mixture was kneaded in a kneading machine for three hours. During the kneading a small portion of the solvent was removed by heating. After the kneading step the paste obtained was recovered from the kneading machine, the remainder of the solvent was removed by heating, and the material was ground and calcined at 500° C.

Hydrocarbon Synthesis Experiments (1–5)

After Catalysts A–E had been activated by means of treatment with a hydrogen-containing gas at 250° C. they were used in the preparation of hydrocarbons from a mixture of carbon monoxide and hydrogen. The experiments were carried out in a reactor containing a fixed catalyst bed. The conditions under which the experiments were carried out and the results of these experiments are given in the table. Of these experiments only Experiments 4 and 5 are part of the invention. Experiments 1–3 fall outside the scope of the invention. They have been included in the patent application for comparison.

Peroxidation Experiment (6)

The $C_{10}$–$C_{19}$ fraction of the product prepared over Catalyst D was treated for 2 hours at 170° C. with 50%w di-tert.butyl peroxide. After distillation of the peroxidated product the 420° C.+ fraction thereof was once again treated for 2 hours at 170° C. with 50 %w di-tert.butyl peroxide. What remained after evaporation of the decomposition products (mainly tert.butyl alcohol and acetone) was an oil having the following properties:

Initial boiling point: 420° C.
Kinematic viscosity at 100° C; 95 cS
Dynamic viscosity at −17.8° C; 120 P
Viscosity index: >200.

Hydro-isomerization Experiment (7)

A sample of the $C_{20+}$ fraction of the product prepared over Catalyst D was contacted together with hydrogen at a temperature of 345° C., a pressure of 130 bar, a space velocity of 1.0 kg.1$^{-1}$.h$^{-1}$ and a H$_2$/hydrocarbon ratio of 2000 N1.1$^{-1}$ with a catalyst comprising 0.82%w of platinum supported on an amorphous silica-alumina having an alumina content of 13%w. The product of the hydrogen treatment was distilled and the 400° C.+ fraction was dewaxed with the aid of a mixture of equal parts by volume of methylethylketone and toluene as solvent, at −30° C. The oil obtained from the filtrate after evaporation of the solvent had the following properties:

Kinematic viscosity at 40° C.: 31.3 cS
Kinematic viscosity at 100° C.: 6.22 cS
VI: 153.

The oil yield was 21%w and the quantity of separated solid paraffins 9%w, both calculated on the $C_{20+}$ fraction used as starting material.

Peroxidation Experiment (8)

An XHVI oil prepared in substantially the same manner as described in Experiment 7 was subjected to a peroxidation treatment in order to increase the viscosity. To this end the oil was treated for 6 hours at 45° C. with 10%w of di-tert.butyl peroxide. After evaporation of the unconverted peroxide and decomposition products such as tert.butyl alcohol and acetone a yield of about 100% of thickened oil was obtained. The properties of the starting material, and those of the thickened oil are given below.

|  | Initial Oil | Thickened Oil |
|---|---|---|
| Kinematic viscosity at 40° C., cS | 32.5 | 54.5 |
| Kinematic viscosity at 100° C., cS | 6.10 | 8.77 |
| VI | 150 | 150 |
| Average molecular weight | 486 | 576 |

Hydro-isomerization Experiment (9)

A sample of the $C_{20+}$ fraction of the product prepared over Catalyst D was contacted together with hydrogen at a temperature of 340° C., a pressure of 130 bar, a space velocity of 2.0 kg.1$^{-1}$.h$^{-1}$ and a H$_2$/hydrocarbon ratio of 2000 N1.1$^{-1}$ with the same Pt/SiO$_2$-Al$_2$O$_3$ catalyst as used in Experiment 7. The total liquid product was subsequently treated for 6 hours, at 145° C., with 10%w di-tert.butyl peroxide. The product was distilled and the 390° C.+ fraction was dewaxed in the same manner as described in Experiment 7. An oil was obtained in 40%w yield, calculated on the $C_{20+}$ fraction used as starting material, which oil had the following properties:

Initial boiling point: 390° C.
Kinematic viscosity at 100° C.: 9.6 cS
Dynamic viscosity at −17.8° C.: 23 P
VI: 141.

Cracking/peroxidation Experiment (10)

A sample of the $C_{20+}$ fraction of the product prepared over Catalyst D was subjected to a mild thermal cracking in the presence of steam at a temperature of 575° C., a pressure of 1 bar, a space velocity of 3.2 kg.1$^{-1}$.h$^{-1}$, calculated on the volume of the cracking zone, a steam dose rate of 6.5%w, calcualted on feed and a nominal residence time in the cracking zone of 2.5 seconds.

From the product thus prepared the $C_{11}$-$C_{12}$ fraction substantially consisting of linear α-oletins was separated and treated with 15%w di-tert.butyl peroxide for 1 hour at 45° C. The reaction product was distilled and the 375° C.+ fraction was dewaxed with the aid of a mixture of equal parts by volume of methylethylketone and toluene as solvent at −30° C. The dewaxed oil, obtained in a yield of about 60%w, calculated on $C_{11}$-$C_{12}$ olefins, had the following properties:

Kinematic viscosity at 100° C.: 34.0 cS
VI: 150.

Upon hydrogenation of this product over a nickel catalyst in order to remove any remaining double bonds, a saturated oil was obtained which had the following properties:

Kinematic viscosity at 100° C.: 35.0 cS
VI: 147.

Peroxidation Experiment (11)

A mixture of 70 pbw of the XHVI oil prepared by the hydro-isomerization Experiment (7) and 30 pbw of a $C_{14}$-$C_{16}$ fraction substantially consisting of linear α-olefins which had been separated from the product obtained in the mild thermal cracking according to Experiment (10) was treated for 6 hours at 145° C. with 10%w di-tert.butyl peroxide. Upon evaporation of unconverted peroxide and decomposition products an oil was obtained which had the following properties:

Kinematic viscosity at 100° C.: 10.3 cS.
VI: 153.

TABLE

| Experiment No. | 1 | 2 | 3 | 4 | 5 |
|---|---|---|---|---|---|
| Catalyst No. | A | B | C | D | E |
| Temperature, °C. | 230 | 320 | 190 | 220 | 204 |
| Pressure, bar | 20 | 20 | 1 | 20 | 20 |
| H$_2$/CO volume ratio | 1.7 | 2.5 | 2.0 | 2.0 | 3.0 |
| Space velocity, N1.1$^{-1}$.h$^{-1}$ | 1750 | 1750 | 75 | 500 | 900 |
| Conversion H$_2$ + CO, % v | 22 | 30 | 70 | 75 | 62 |
| Product distribution, % w |  |  |  |  |  |
| Gas (C$_1$-C$_4$) | 22.6 | 54.1 | 28.5 | 18.0 | 23.0 |
| Gasoline (C$_5$−200° C.) | 28.3 | 31.9 | 42.5 | 15.1 | 19.0 |
| Kerosine + gas oil (200-350° C.) | 19.5 | 2.5 | 19.5 | 28.4 | 22.4 |
| Waxy residue (350° C.+) | 26.4 | 0 | 8.0 | 38.0 | 35.4 |
| Water-soluble oxygen compounds | 3.4 | 11.3 | 1.5 | 0.5 | 0.2 |
| Properties of C$_5$ + product |  |  |  |  |  |
| Olefins content, % mol | 50 | 80 | 34 | 8 | 2 |
| Aromatics content, % mol | 0.3 | 5.0 | 0.1 | 0 | 0 |
| Linearity, % (percentage linear paraffins and olefins calculated on total of paraffins and olefins) | 90 | 50 | 60 | 95 | 97 |
| Number of C atoms in tertiary structure, % | 1 | 5 | 4 | 0.2 | 0.1 |

What is claimed is:

1. A process for the preparation of a high-viscosity-index lubricating oil, wherein a feed mixture of carbon monoxide and hydrogen is converted into a mixture of hydrocarbons substantially consisting of linear paraffins, by contacting said feed mixture at elevated temperature and pressure with a catalyst comprising 3–60 pbw of cobalt and 0.1–100 pbw of at least one other metal selected fom the group consisting of zirconium, titanium and chromium per 100 pbw of silica, alumina or silica-alumina carrier, which catalyst has been prepared by kneading and/or impregnation, that from the mixture of paraffins thus prepared a light fraction is separated which consists substantially of $C_{10}$–$C_{19}$ paraffins, and that at least part of said light fraction is converted into a product comprising the desired high-viscosity-index lubricating oil by treating it at an elevated temperature with a peroxide of the general formula R-O-O-R$^1$, wherein R and R$^1$ represent alkyl, aryl or acyl moieties.

2. The process of claim 1 wherein a $H_2/CO$ mixture is used which has been obtained, starting from light hydrocarbons, by steam reforming or partial oxidation.

3. The process of claim 1 wherein a $H_2/CO$ mixture is used which has been obtained starting from natural gas.

4. The process of claim 1 wherein said catalyst satisfies the relation $$(3+4R) > (L/S) > (0.3+0.4R),$$

wherein
- L = the total quantity of cobalt present on the catalyst, expressed as mg Co/ml catalyst,
- S = the surface area of the catalyst, expressed as $m^2$/ml catalyst, and
- R = the weight ratio of the quantity of cobalt deposited on the catalyst by kneading to the total quantity of cobalt present on the catalyst.

5. The process of claim 4 wherein said catalyst comprises per 100 pbw of carrier, 14–50 pbw of cobalt and either 0.5–5 pbw of the other metal when during the preparation cobalt was deposited first and the other metal next, or 5–40 pbw of the other metal when during the preparation the other metal was deposited first and cobalt next.

6. The process of claim 5 wherein said catalyst comprises zirconium as other metal and silica as carrier.

7. The process of claim 1 wherein the conversion of the $H_2/CO$ mixture is carried out at a temperature of 125°–350° C. and a pressure of 50–100 bar.

8. The process of claim 7 wherein the conversion of the $H_2/CO$ mixture is carried out at a temperature of 175°–275° C. and a pressure of 10–75 bar.

9. The process of claim 1 wherein the peroxide used is a di-tert.alkyl peroxide having 8–20 carbon atoms per molecule.

10. The process of claim 9 wherein the peroxide used is di-tert.butyl peroxide.

11. The process of claim 1 wherein the quantity of peroxide used is at least 10%w and not more than 150%w, calculated on the quantity of paraffins to be treated.

12. The process of claim 11 wherein the quantity of peroxide used is not more than 100%w, calculated on the quantity of paraffins to be treated.

13. The process of claim 1 wherein the reaction time and reaction temperature of the peroxide treatment are between 5 minutes and 10 hours, and between 100° and 225° C., respectively.

14. The process of claim 1 wherein the peroxide treatment is carried out over such a reaction time and at such a reaction temperature that at least 90%w of the peroxide has decomposed at the moment of termination of the treatment.

15. The process of claim 14 wherein the peroxide treatment is carried out over such a reaction time and at such a reaction temperature that at least 95%w of the peroxide has decomposed at the moment of termination of the treatment.

16. The process of claim 15 wherein the peroxide treatment is carried out in several steps.

17. The process of claim 16 wherein the light paraffin fraction is treated with peroxide, the peroxide-treated product is divided by distillation into a light fraction and a heavy fraction whose initial boiling point lies above the final boiling point of the light paraffin fraction to be peroxidated and the heavy fraction is treated one or more times with peroxide.

18. The process of claim 16 wherein the light paraffin fraction is treated with peroxide, the peroxide-treated product is divided by distillation into a light fraction and a heavy fraction whose initial boiling point lies above the final boiling point of the light paraffin fraction to be peroxidated, the light fraction is again treated with peroxide, the heavy fractions obtained by distillation from the peroxide-treated products are combined, and the combined mixture is treated one or more times with peroxide.

* * * * *